US00PP21856P2

(12) United States Plant Patent
Egger

(10) Patent No.: US PP21,856 P2
(45) Date of Patent: Apr. 5, 2011

(54) ***HEUCHERA* PLANT NAMED 'ELECTRA'**

(50) Latin Name: ***Heuchera* hybrid**
Varietal Denomination: Electra

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 58 days.

(21) Appl. No.: 12/653,586

(22) Filed: Dec. 14, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner* — Kent L Bell
(74) *Attorney, Agent, or Firm* — Klarquist Sparkman, LLP

(57) ABSTRACT

A new and distinct hybrid of *Heuchera* plant characterized by medium gold spring leaves, lime colored leaves with red veins in the summer and fall, amber to rust colored leaves with red veins in the winter, a compact habit, excellent vigor, and excellent tolerance to heat and humidity.

2 Drawing Sheets

Botanical denomination: *Heuchera* Hybrid.
Variety designation: 'Electra'.
Cross Reference to sibling: *Heuchera* 'Electric Lime' (U.S. Plant patent application Ser. No. 12/653,633)

BACKGROUND OF THE INVENTION

The present invention relates to a new and distinct cultivar of *Heuchera* hybrid and given the cultivar name of 'Electra'. *Heuchera* is in the family Saxifragaceae. *Heuchera* 'Electra' originated from a cross between *Heuchera* 'Southern Comfort' (U.S. Plant Pat. No. 20,364) as the seed parent, and *Heuchera* 426-2, a proprietary unreleased plant, as the pollen parent.

This new *Heuchera* is distinguished by:

1. medium gold spring leaves,
2. lime colored leaves with red veins in the summer and fall,
3. amber to rust colored leaves with red veins in the winter,
4. white flowers on a short flowering stem,
5. a compact habit,
6. excellent vigor, and
7. excellent tolerance to heat and humidity.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a one-year-old plant of *Heuchera* 'Electra' growing in a one gallon pot in the summer in Canby, Oreg.

FIG. 2 shows a one gallon size plant in bloom in May.

DETAILED PLANT DESCRIPTION

Figure 3:
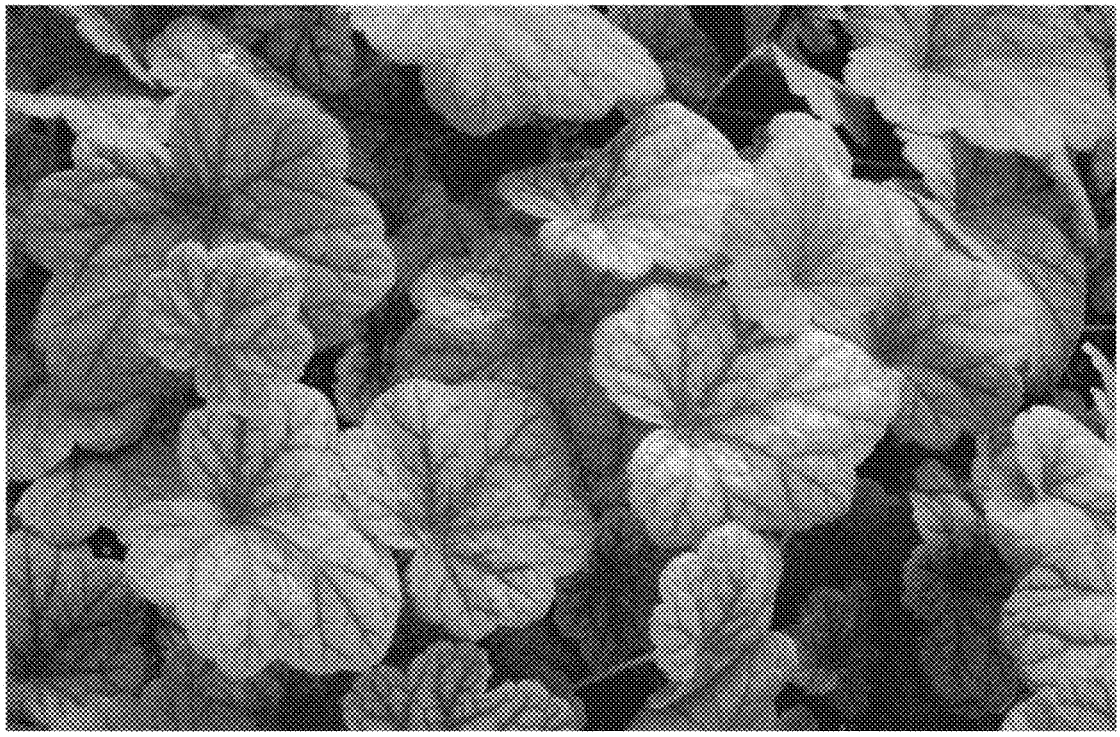
FIG. 3 shows the foliage winter color.

The following is a detailed description of the new *Heuchera* cultivar based on observations taken in May of a one-year-old specimen grown in a one gallon container in a cool greenhouse in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 1999 edition.

Plant:

*Form.*—Basal rosette, herbaceous perennial.
*Hardiness.*—USDA Zone 4 to 9.
*Size.*—18 cm tall from top of the foliage to the ground and 29 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Rosette.
*Shape.*—Broadly ovate.
*Lobing/division.*—7 shallow lobes, the terminal is the longest.
*Venation.*—Palmate.
*Margins.*—Crenate.
*Apex.*—Mucronulate.
*Base.*—Cordate, lobes sometimes overlapping at the base.
*Blade size.*—10 cm to 13 cm long and 9 cm to 12.5 cm wide.
*Surface texture.*—Glandular on both sides.
*Petiole description.*—10 cm to 11 cm long and 2 mm wide, glandular hairs, Greyed Red 182B to Greyed Orange 177D.
*Leaf color.*—Variable depending amount of light, temperature, and age of the leaf; spring new growth topside between Yellow Green 145A and Yellow Green 144A, bottom side. Yellow Green 145C; older leaves are more yellow, Yellow 11A with red veins Greyed Purple 183B, bottom side closest to Green Yellow 1D with veins Greyed Red 182C; winter topside is dull lime green (between Yellow Green 144A and Greyed Green 195A) or rust (closest to Greyed Orange 172B) with veins Greyed Purple 187A, bottom side Greyed Purple 186B.

Inflorescence:

*Size.*—Grows to 12 cm long and 3 cm wide.

*Type.*—Thyrse.

*Number of flowers per thyrse.*—About 70 per thyrse.

*Number of thyrse.*—About 5 to 7 in spring bloom.

*Peduncle.*—Grows to 28 cm tall, 3 mm wide at base, Yellow Green 152C, prominent glandular hairs, with no substantial cauline leaves.

*Pedicel.*—Variable in size, with glandular hairs, Yellow Green 151 A.

*Bloom period.*—Late May to June in Canby, Oreg.

Flower bud:

*Size.*—2 mm wide and 3 mm long.

*Description.*—Glandular puberulent, ovoid.

*Color.*—White 155A on top half and Yellow Green 145A on bottom half

Flower:

*Type.*—Perfect.

*Shape.*—Campanulate.

*Size.*—5 mm long and 4 mm wide.

*Petal description.*—5 in number, inconspicuous, 2.5 mm long, spatulate, tip obtuse, margin entire, glabrous on both sides, White 155D on both sides.

*Calyx description.*—Campanulate, 5 mm long and 4 mm wide, with 5 lobes, divided ⅓ way to the base, glandular hairs on outside, glabrous inside; lobes inside and out White 155A except at tip Yellow Green 145A, acute, entire, Yellow Green 145A below lobes.

*Stamen description.*—5 in number, filaments 3 mm long, White 155D, anthers sterile, 0.5 mm, Greyed Orange 174D.

*Pistil description.*—1, 2-beaked, 4 mm long, ovary 1 mm, White 155D, style 3 mm long, White 155D.

*Fragrance.*—None.

*Lastingness.*—Each thyrse blooms for about 2 weeks on the plant.

Fruit:

*Type.*—Two beaked capsule.

*Size.*—3.5 mm deep by 5 mm wide.

*Fertility.*—Good.

*Color.*—Brown 200D.

Seed:

*Shape.*—Linear.

*Size.*—2 mm long.

*Color.*—Black, RHS 202A.

Pest and disease tolerance: Excellent disease resistance to powdery mildew, the common problem of *Heuchera*. Susceptible to *Heuchera* rust and root weevils.

COMPARISON TO SIMILAR *HEUCHERA*

Compared to the seed parent, *Heuchera* 'Southern Comfort', the new hybrid has a smaller habit, shorter flower stems, and leaves that are gold to lime green with red veins rather than amber.

Compared to the pollen parent *Heuchera* 426-2, the new hybrid has larger leaves with stronger pubescence and lime to gold rather than green leaves.

Compared to *Heuchera* 'Tiramisu' (U.S. Plant Pat. No. 20,429) the new variety has bigger leaves with red veins summer, fall and winter, rather than a red pattern in spring and fall.

Compared to *Heuchera* 'Electric Lime' (U.S. Plant patent application Ser. No. 12/653,633), the new variety has smaller leaves, a compact habit, and more red in the veins.

I claim:

1. A new and distinct hybrid of *Heuchera* plant as herein illustrated and described.

* * * * *

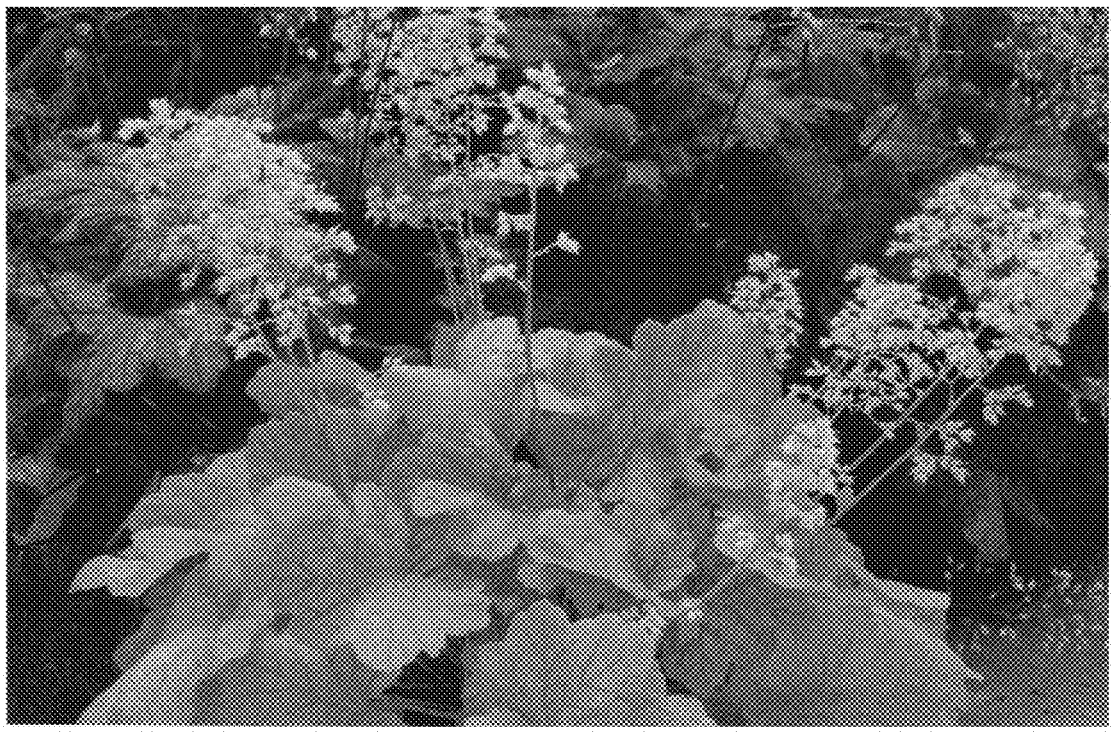

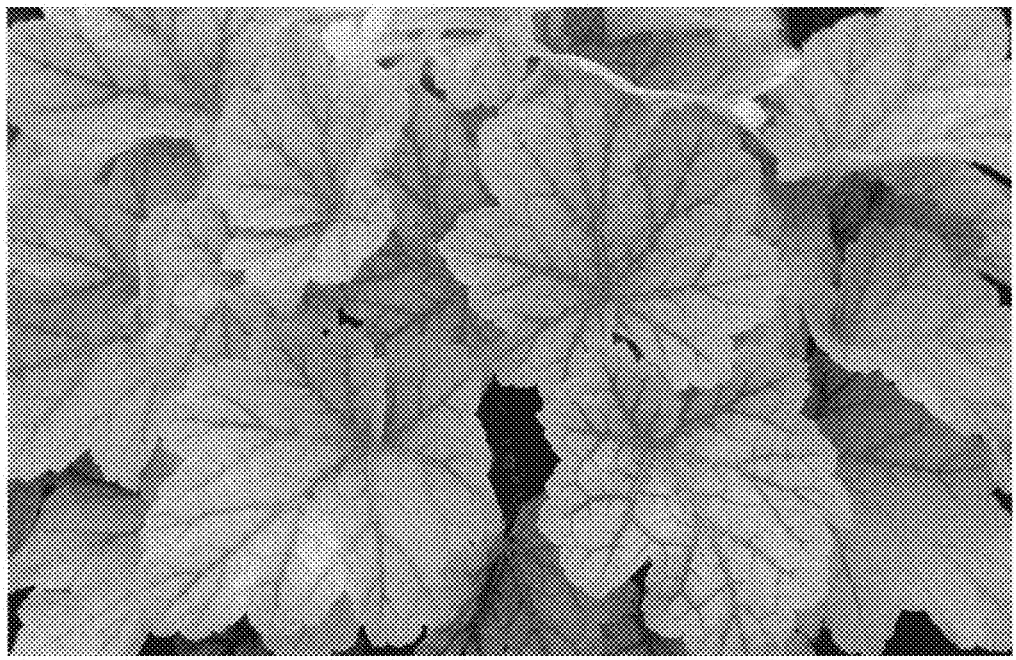
Figure 1 above, Figure 2 below